(12) United States Patent
Amako et al.

(10) Patent No.: US 8,553,220 B2
(45) Date of Patent: Oct. 8, 2013

(54) OPTICAL DEVICE AND ANALYZING APPARATUS

(75) Inventors: Jun Amako, Matsumoto (JP); Kohei Yamada, Minowa (JP)

(73) Assignee: Seiko Epson Corporation (JP)

( * ) Notice: Subject to any disclaimer, the term of this patent is extended or adjusted under 35 U.S.C. 154(b) by 216 days.

(21) Appl. No.: 13/106,554

(22) Filed: May 12, 2011

(65) Prior Publication Data

US 2011/0279817 A1     Nov. 17, 2011

(30) Foreign Application Priority Data

May 13, 2010   (JP) ................................. 2010-111144

(51) Int. Cl.
*G02B 5/30* (2006.01)
*G01J 3/44* (2006.01)

(52) U.S. Cl.
USPC ...................... 356/301; 359/569; 359/486.01

(58) Field of Classification Search
USPC ........... 356/301; 359/486.01–486.02, 487.03, 359/566–576
See application file for complete search history.

(56) References Cited

U.S. PATENT DOCUMENTS

| | | | |
|---|---|---|---|
| 5,986,762 A | 11/1999 | Challener | |
| 7,722,194 B2 | 5/2010 | Amako et al. | |
| 7,755,718 B2 | 7/2010 | Amako et al. | |
| 7,885,004 B2 | 2/2011 | Amako et al. | |
| 8,274,739 B2 * | 9/2012 | Lee et al. | 359/585 |
| 2006/0273245 A1 | 12/2006 | Kim et al. | |
| 2008/0304004 A1 | 12/2008 | Amako et al. | |
| 2010/0020400 A1 | 1/2010 | Amako | |
| 2010/0188747 A1 | 7/2010 | Amako et al. | |
| 2011/0267613 A1 * | 11/2011 | Amako et al. | 356/301 |

FOREIGN PATENT DOCUMENTS

| | | |
|---|---|---|
| JP | 2007-240361 | 9/2007 |
| JP | 2009-015302 | 1/2009 |
| JP | 2009-015305 | 1/2009 |
| JP | 2009-064005 | 3/2009 |
| JP | 2009-134287 | 6/2009 |
| WO | 2008-114148 | 9/2008 |
| WO | 2009-119391 | 10/2009 |

OTHER PUBLICATIONS

European Search Report for Application No. 11 16 5661 dated Oct. 4, 2011 (6 pages).

Lifeng Li and Charles W. Haggans, "Convergence of the coupled-wave method for metallic lamellar diffraction gratings", J. Opt. Soc. Am. A, vol. 10, No. 6/Jun. 1993 (pp. 1184-1189).

* cited by examiner

*Primary Examiner* — Layla Lauchman
(74) *Attorney, Agent, or Firm* — Harness, Dickey & Pierce, P.L.C.

(57) ABSTRACT

An optical device includes a projection group in which electrically conductive projections are arranged along a direction parallel to a virtual plane. The arrangement period of the projections in the projection group includes at least a first period and a second period different from the first period. The first period and the second period are shorter than a wavelength of an incident light.

16 Claims, 15 Drawing Sheets

Comparative Example

Comparative Example

Comparative Example

OPTICAL DEVICE AND ANALYZING APPARATUS

This application claims priority to Japanese Patent Application No. 2010-111144 filed May 13, 2010 which is hereby expressly incorporated by reference herein in its entirety.

BACKGROUND

1. Technical Field

The present invention relates to an optical device and an analyzing apparatus.

2. Related Art

In recent years, the demand for a sensor used for medical diagnosis, food inspection or the like has increased, and the development of a highly sensitive small sensor has been requested. In order to meet such request, various types of sensors including one using an electrochemical technique have been studied. Among these, interest in a sensor using surface plasmon resonance has increased because the sensor can be integrated, manufactured at low cost, and used in any measurement environment.

For example, JP-A-2007-240361 discloses a surface plasmon resonance sensor in which light is coupled to a surface plasmon polariton by a metal periodic structure.

However, in this sensor, since the resonant condition of the surface plasmon has a large selectivity to an incident angle of light, only light of a specific incident angle is coupled to the surface plasmon polariton. Thus, only apart of the light concentrated by an objective lens is coupled to the surface plasmon polariton, and there is a problem in that a sufficient sensing sensitivity cannot be obtained.

SUMMARY

An advantage of some aspects of the invention is to provide an optical device in which the coupling efficiency of light to a surface plasmon polariton can be improved.

One aspect of the invention relates to an optical device that includes a projection group in which electrically conductive projections are arranged along a direction parallel to a virtual plane. An arrangement period of the projections in the projection group includes at least a first period and a second period different from the first period. The first period and the second period are shorter than a wavelength $\lambda 1$ of an incident light.

According to this aspect of the invention, the electrically conductive projections are arranged along the direction parallel to the virtual plane. The arrangement period of the projections includes at least the first period and the second period shorter than the wavelength $\lambda 1$ of the incident light. As a result, the coupling efficiency of the light to the surface plasmon polariton can be improved.

This aspect of the invention may be configured such that the projection group includes a first projection group arranged at the first period and a second projection group arranged at the second period, the first projection group is provided in a first area, and the second projection group is provided in a second area adjacent to the first area.

This aspect of the invention may be configured such that the projection group includes a first projection group arranged at a first variable period which increases or decreases stepwise from the first period, and a second projection group arranged at a second variable period which increases or decreases stepwise from the second period, the first projection group is provided in a first area and the second projection group is provided in a second area adjacent to the first area.

This aspect of the invention may be configured such that the period of the first projection group and the period of the second projection group increases or decreases stepwise between the first area to the second area.

According to the optical device as described above, the projection group can be arranged at the period including the first period and the second period different from the first period.

This aspect of the invention may be configured such that the incident light includes a light incident at a first angle with respect to a vertical line directed to the virtual plane and a light incident at a second angle different from the first angle with respect to the vertical line directed to the virtual plane. The light incident at the first angle is incident on the projections arranged at the first period, and the light incident at the second angle is incident on the projections arranged at the second period. A material of the projection group, the first period, the second period, the first angle and the second angle are set so that a resonant wavelength of surface plasmon resonance at the projections arranged at the first period and a resonant wavelength of surface plasmon resonance at the projections arranged at the second period become the wavelength $\lambda 1$.

By doing this, the resonant wavelength of the surface plasmon resonance at the projections arranged at the first period and the resonant wavelength of the surface plasmon resonance at the projections arranged at the second period can be made the wavelength equal to the wavelength $\lambda 1$ of the incident light. As a result, the incident light of the first incident angle and the incident light of the second incident angle can be coupled to the surface plasmon polariton.

This aspect of the invention may be configured such that the first period is longer than the second period.

This aspect of the invention may be configured such that the first period is shorter than the second period.

According to the optical device as described above, the magnitude relation between the first period and the second period can be set. As a result, the propagation direction of the surface plasmon polariton can be adjusted.

This aspect of the invention may be configured such that the projection group is arranged in the same arrangement direction.

***This aspect of the invention may be configured such that the projection group is arranged in a stripe shape, and the arrangement direction of the projection group is the same linear direction over the entire stripe arrangement.

This aspect of the invention may be configured such that the projection group is arranged concentrically, and the arrangement direction of the projection group is a radial direction of the concentric arrangement.

According to the optical device as described above, the projection group can be arranged in the same arrangement direction along the direction parallel to the surface of the base member.

This aspect of the invention may be configured such that the arrangement direction of the projection group is the same direction as a polarization direction of the incident light.

This aspect of the invention may be configured such that the incident light is a linearly polarized light, and the arrangement direction of the projection group is equal to the polarization direction of the linearly polarized light.

This aspect of the invention may be configured such that the incident light is a radially polarized light, and the arrangement direction of the projection group is equal to the polarization direction of the radially polarized light.

According to the optical device as described above, the projection group can be arranged along the same direction as the polarization direction of the incident light.

This aspect of the invention may be configured such that a first small projection group of electric conductors is provided on a top surface of the projection group, and an interval between projections of the first small projection group is shorter than the arrangement period of the projections in the projection group.

By doing this, the first small projection group can be formed on the top surface of the projection group. As a result, a localized surface plasmon can be excited in the first small projection group.

This aspect of the invention may be configured such that a second small projection group of electric conductors is provided on a surface parallel to the virtual plane and between the adjacent projections of the projection group, and an interval between the projections in the second small projection group is shorter than the arrangement period of the projections in the projection group.

By doing this, the second small projection group can be formed between the adjacent projections of the projection group. As a result, the localized surface plasmon can be excited in the second small projection group.

Another aspect of the invention relates to an analyzing apparatus including a light source, the above-described optical device, a first optical system that concentrates a light of the wavelength $\lambda 1$ from the light source to the projection group, and causes the incident light including at least a component incident at a first angle with respect to a vertical line directed to the virtual plane and a component incident at a second angle different from the first angle to be incident on the projection group, a second optical system to extract Raman scattering light from light scattered or reflected by a diffraction grating of the optical device, and a detector to detect the Raman scattering light received through the second optical system.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described in detail. Incidentally, the embodiments described below do not limit the scope of the invention recited in the claims, and all components described in the embodiments are not necessarily indispensable to the invention.

1. COMPARATIVE EXAMPLE

As described before, a surface plasmon resonance sensor using a metal periodic structure has a problem in that the selectivity of the surface plasmon resonance is high with respect to the incident angle of the incident light. This point will be specifically described with reference to FIG. 1A to FIG. 4.

Figure 1A:
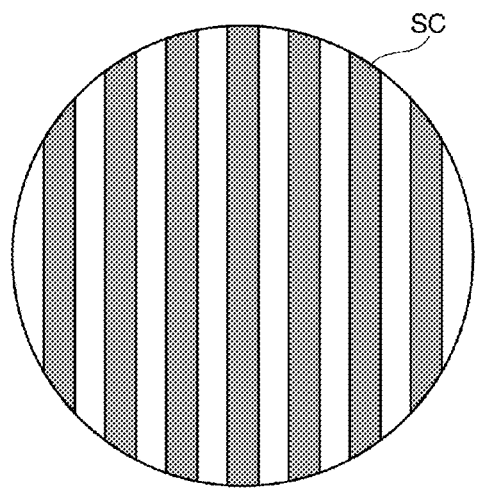
FIG. 1A and FIG. 1B show a comparative example of a sensor chip.
Figure 1B:
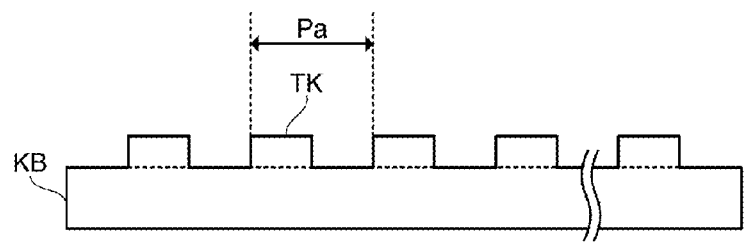

FIG. 1A and FIG. 1B show a comparative example of a sensor chip (optical device) of an embodiment. FIG. 1A is a plan view of the sensor chip, and FIG. 1B is a sectional view of the sensor chip. As shown in FIG. 1A, a metal periodic structure including one-dimensional convex-concave structures are formed in the sensor chip SC (shaded portion represents a projection part of the periodic structure). Specifically, as shown in FIG. 1B, a projection group TK is arranged at a period Pa in a direction along a plane of a base member KB of the sensor chip SC.

In the sensor chip SC, light is coupled to a surface plasmon polariton (SPP) by the metal periodic structure. The excited surface plasmon polariton generates an enhanced electric field in the vicinity of the surface of the metal periodic structure, and the enhanced electric field acts on a target attached to the sensor surface and causes surface-enhanced Raman scattering. The scattered light spectrum caused by the surface-enhanced Raman scattering is acquired so that the target (a specific material) is detected.

Figure 2:
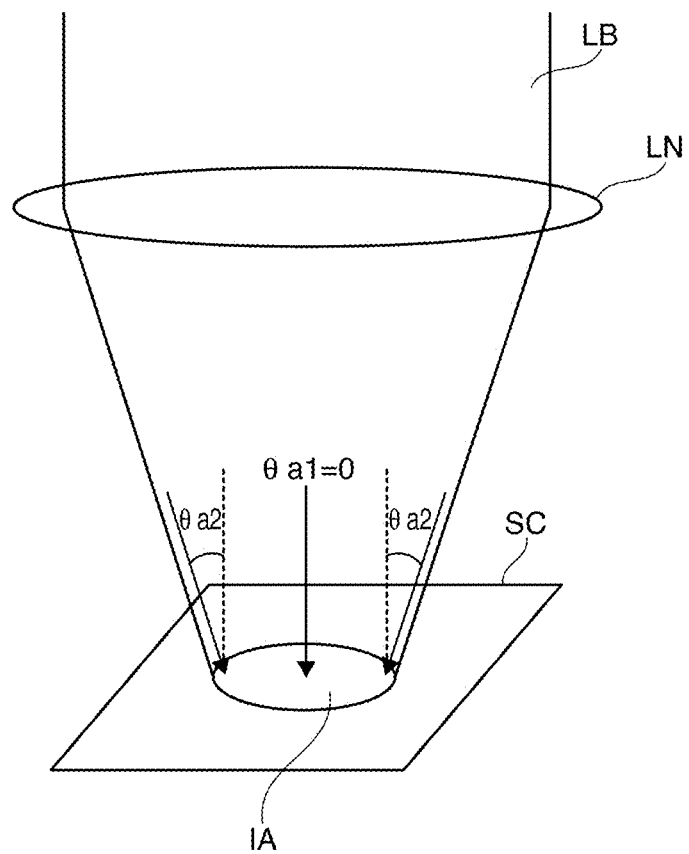
FIG. 2 is an explanatory view of an incident angle of incident light.

As shown in FIG. 2, a laser light LB concentrated by an objective lens LN is emitted as an incident light to the sensor chip SC. When the light is concentrated by the objective lens LN, the light beam is incident on an irradiation area IA of the laser light LB at various angles. For example, the light beam is incident at $\theta a1=0°$ along the optical axis, and a light beam is incident at $\theta a2 \neq \theta a1$ onto the outer periphery of the irradiation area IA. At this time, in the sensor chip SC, since the light incident angle selectivity of the surface plasmon resonance (SPR) due to the metal periodic structure is high, only a light having a specific angle component (for example, $\theta a1=0°$) is coupled to the surface plasmon polariton. This point will be described with reference to FIG. 3 and FIG. 4.

Figure 3:
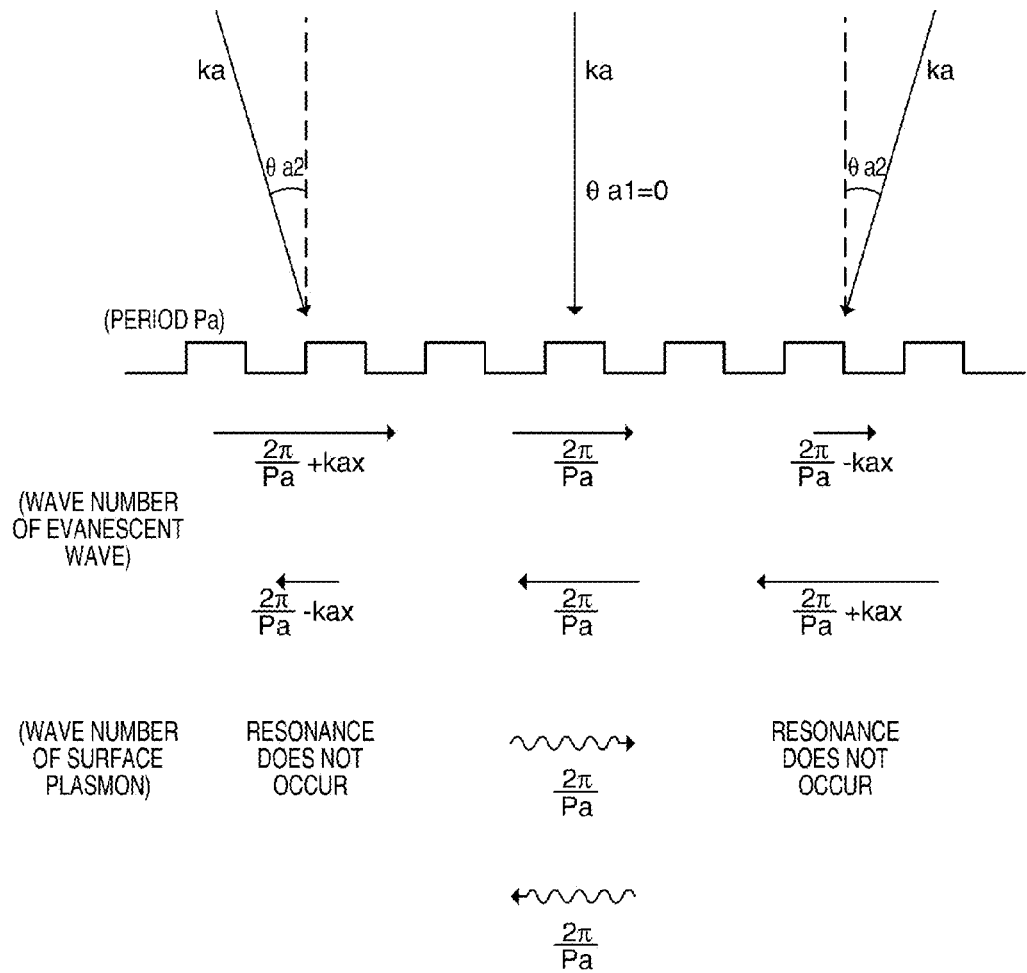
FIG. 3 is a schematic explanatory view of surface plasmon resonance in the comparative example.

FIG. 3 is a schematic explanatory view of surface plasmon resonance in the comparative example. As shown in FIG. 3, it is assumed that the light of wave number Ka is incident at θa1=0° and θa2>0° onto the metal grating of a period Pa. Then, an evanescent wave of wave number 2π/Pa is generated in response to the incident light of θa1=0° by the diffraction condition of the metal grating, and an evanescent wave of wave number 2π/Pa±kax is generated in response to the incident light of θa2>0°. Here, kax=ka·sin θa2.

For example, it is assumed that the surface plasmon polariton is coupled to the evanescent wave of wave number 2π/Pa. Then, the surface plasmon (SP) of wave number 2π/Pa is excited by the incident light of θa1=0°. On the other hand, in the incident light of θa2>0°, the evanescent wave of wave number 2π/Pa±kax is not coupled to the surface plasmon polariton, and the surface plasmon is not excited.

Figure 4:
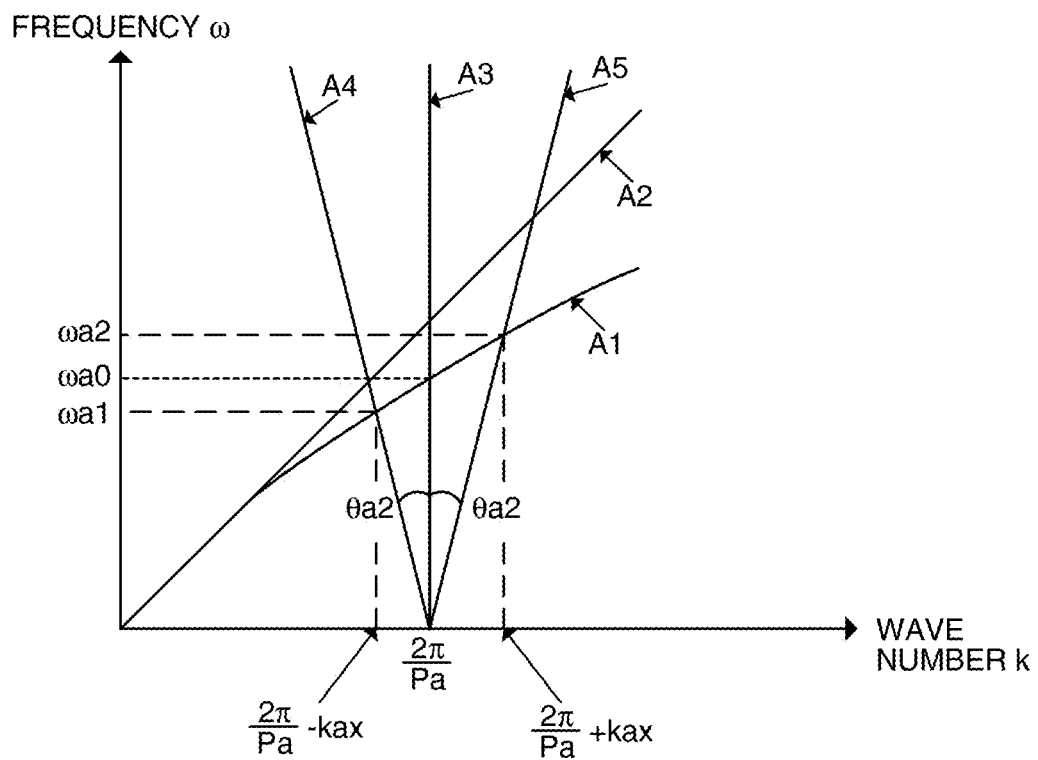
FIG. 4 shows a dispersion curve of surface plasmon polariton in the comparative example.

FIG. 4 shows a dispersion curve of surface plasmon polariton in the comparative example. Reference numeral A1 denotes the dispersion curve, A2 denotes a light line, A3 denotes a straight line representing the diffraction condition in the case of θa1=0°, and A4 and A5 denote straight lines representing the diffraction condition in the case of θa2>0°. The resonant condition is represented by an intersection point between the straight lines A3 to A5 representing the diffraction conditions and the dispersion curve A1. That is, in the case of θa1=0°, resonance occurs at the incident light of frequency ω0, and in the case of θa2>0°, resonance occurs at the incident light of frequency ω1, ω2≠ω0. Accordingly, when the laser light LB has the single frequency ω0, only the incident light of the specific incident angle θa1=0° is coupled to the surface plasmon polariton of the wave number 2π/Pa.

As stated above, in the sensor chip of the comparative example, since only the light incident at the specific angle (for example, vertical incidence θa1=0°) is coupled to the surface plasmon polariton, the surface plasmon resonance occurs only in a part of the sensor chip. Thus, the coupling efficiency of the light to the surface plasmon polariton becomes very low, and this is a problem in sensing a faint Raman scattering light at high sensitivity.

2. STRUCTURAL EXAMPLE

In this embodiment, metal gratings are formed which are different in period according to the incident angle of the incident light, so that the coupling efficiency of the incident light to the surface plasmon polariton is improved, and the sensing sensitivity of the surface-enhanced Raman scattering is improved. The sensor chip (optical device, metal grating) of this embodiment will be described with reference to FIG. 5A to FIG. 7. Incidentally, in the following, in order to cause the sizes of respective components to become such that they can be recognized in the drawings, the sizes and ratios of the respective components are suitably made different from actual ones.

In the following, although a description will be made of the case where the sensor chip is used for surface-enhanced Raman scattering spectrum, the embodiment is not limited to this case, and enhanced electric field by the sensor chip can be used for various spectrum methods. Further, in the following, although a description will be made of the case where the sensor chip is a metal grating made of a metal, the embodiment is not limited to this case. That is, the sensor chip may be a grating made of any electric conductor, and may be a grating made of, for example, a semiconductor material (for example, polysilicon).

Figure 5A:
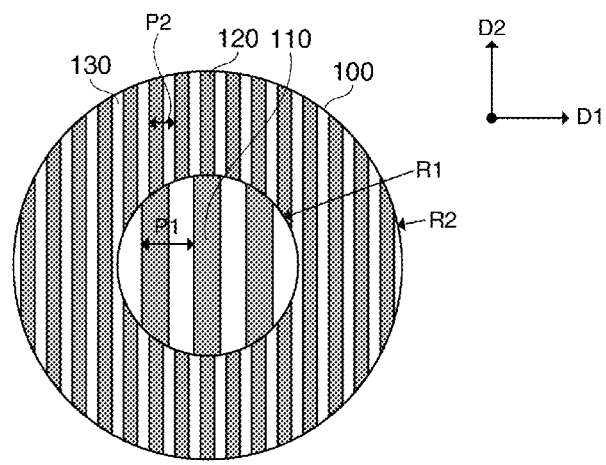
FIG. 5A is a plan view of a structural example of a sensor chip of an embodiment.

FIG. 5A is a plan view of a structural example of the sensor chip of the embodiment. The sensor chip is for detecting a target (target material, target molecule) by using the surface plasmon resonance and the surface-enhanced Raman scattering, and includes a base member 100 (substrate), a first projection group 110 and a second projection group 120. The sensor chip is a diffraction grating having a one-dimensional periodic structure.

Specifically, the base member 100 includes a metal (a conductor in abroad sense), and is formed into, for example, a circular or square flat plate. The first projection group 110 is formed in a first area R1, and is arranged at a period P1 along a first direction D1 parallel to a plane (surface in a broad sense) of the base member 100. The second projection group 120 is formed in a second area R2, and is arranged along the direction D1 at a period P2 (P1>P2 or P1<P2) different from the period P1. Here, the plane of the base member 100 is a surface parallel to a surface 130 of the base member 100 at the side where the projection group is formed. For example, the first projection group 110 and the second projection group 120 are formed in a stripe shape parallel to a second direction D2 perpendicular to the direction D1 when the base member 100 is viewed in plane.

Figure 5B:
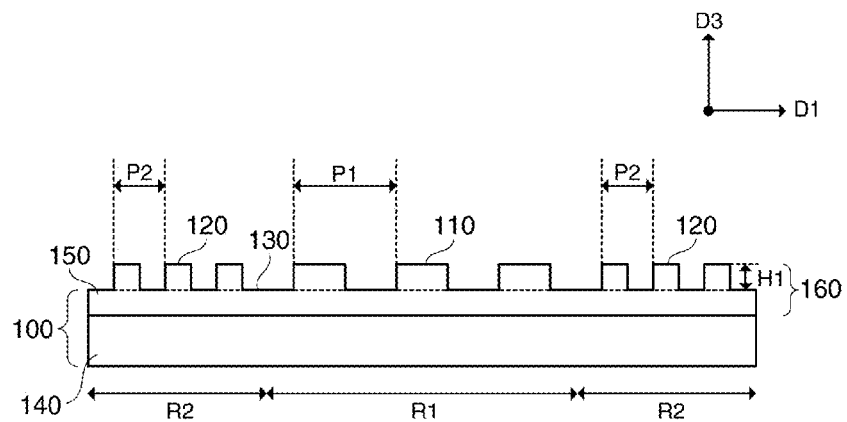
FIG. 5B is a sectional view of the structural example of the sensor chip of the embodiment.

FIG. 5B is a sectional view of a structural example of the sensor chip of the embodiment. The section of the sectional view is a surface vertical to the plane of the base member 100 and is a surface parallel to the arrangement direction D1 of the projection groups 110 and 120. As shown in FIG. 5B, a normal direction of the plane of the base member 100 is a direction D3.

The base member 100 is such that a metal thin film 150 is formed on a glass substrate 140. The first projection group 110 is made of a metal of a first material, and the second projection group 120 is made of a metal of a second material. A metal grating 160 includes the metal thin film 150, the first projection group 110, and the second projection group 120. The metal of the first and the second material is, for example, the metal of the same material as the metal thin film 150, and Ag (silver), Au (gold), Pt (platinum), Cu (copper), Al (aluminum) or the like or an alloy of these is used. The sectional shape of the first projection group 110 and the second projection group 120 is a convex shape having a height H from the surface 130 of the base member 100. The convex shape is, for example, a rectangle (including a substantial rectangle), or may be a trapezoid, an arc or the like. As a manufacturing method of the metal grating 160, electron beam lithography or nano-in-print can be used.

Incidentally, in the structural example, although the case where the two metal concave-convex structures different in period are arranged in the concentrically divided areas R1 and R2 is exemplified, this embodiment is not limited to the case where the area R2 as shown in FIG. 5A surrounds the area R1. For example, in this embodiment, two areas R2 may be arranged along the direction D1, and the area R1 may be arranged between the two areas R2.

3. SETTING METHOD OF THE PERIODS P1 AND P2

Figure 6:
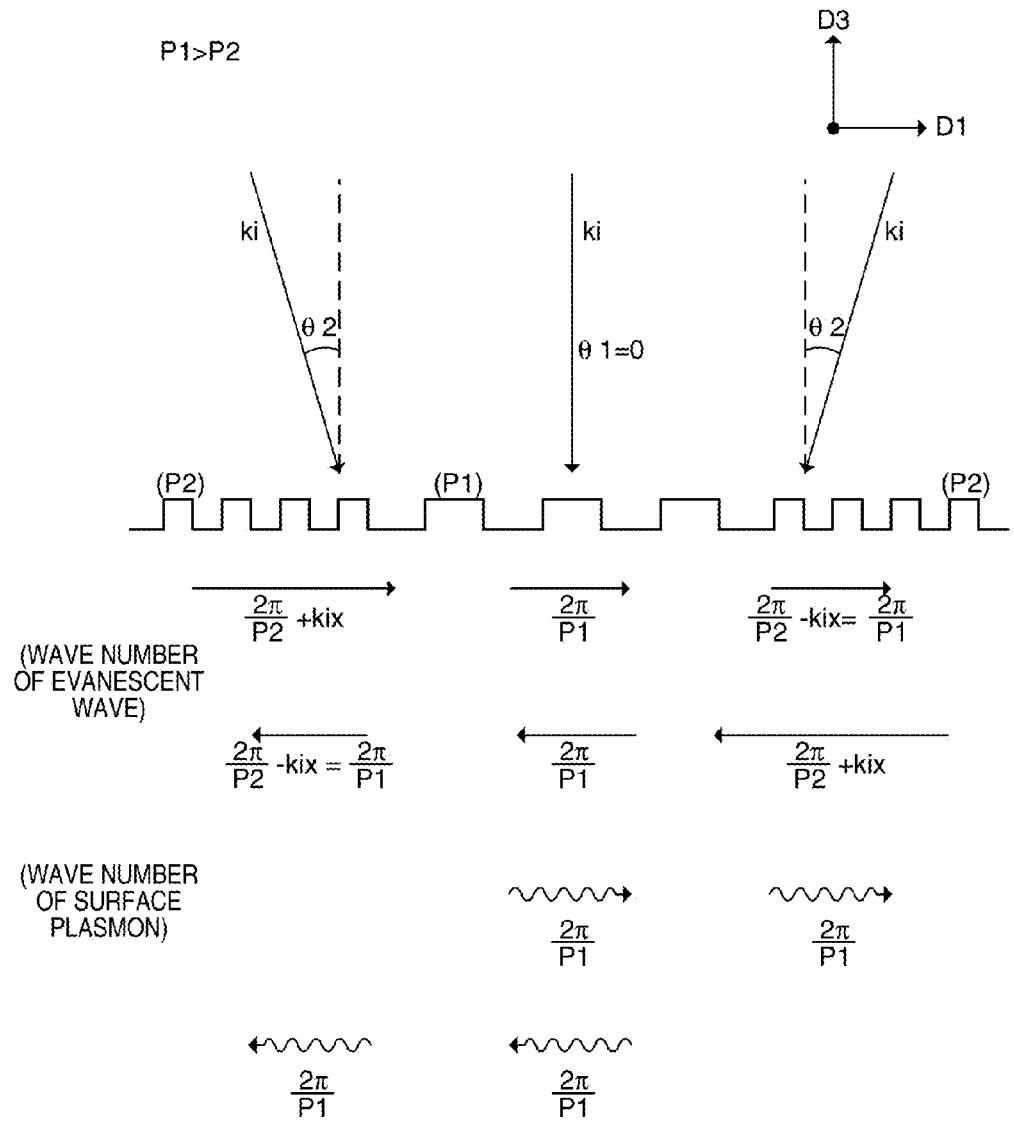
FIG. 6 is a schematic explanatory view of surface plasmon resonance in the case of P1>P2.
Figure 14:
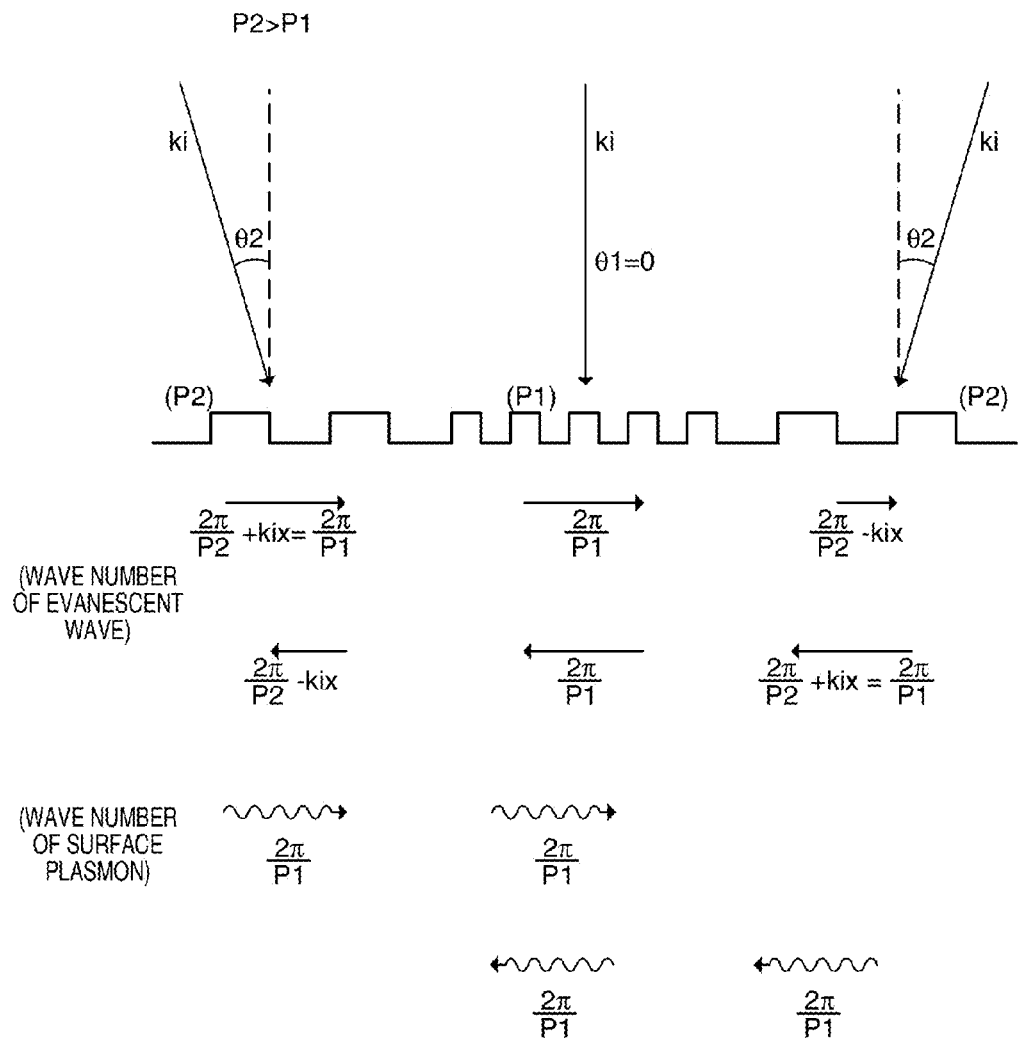
FIG. 14 is a schematic explanatory view of surface plasmon resonance in the case of P1<P2.

Next, a setting method of the periods P1 and P2 in this embodiment will be described. First, the function of the sensor chip of the embodiment will be described. FIG. 6 is a schematic explanatory view of surface plasmon resonance in the case of P1>P2. In the following, although the case of P1>P2 will be exemplified, P1<P2 may be adopted as shown in FIG. 14.

As shown in FIG. 6, it is assumed that the wave number of the incident light is ki, the incident light is incident on the grating of the period P1 at θ1=0°, and the incident light is incident on the grating of the period P2 at θ2>0°. Then, by the diffraction condition of the metal grating, an evanescent wave of wave number 2π/P1 is generated in the grating of the period P1, and an evanescent wave of wave number $2\pi/P2 \pm kix$ is generated in the grating of the period P2. Here, $kix = ki \cdot \sin\theta2$. The incident angle of the incident light is an angle between the direction (vertical line directed to the base member plane) opposite to the normal direction D3 of the base member plane and the incident light.

In this embodiment, the periods P1 and P2 are set so as to satisfy $2\pi/P2 - kix = 2\pi/P1$. Further, the period P1 is set so that the surface plasmon polariton is coupled to the evanescent wave of the wave number $2\pi/P1$. Then, both incident lights having the incident angles θ1 and θ2 and the surface plasmon polariton are coupled, and the surface plasmon of the wave number $2\pi/P1$ is excited at both gratings having the periods P1 and P2. Incidentally, as shown in FIG. 6, when the sensor chip is arranged at a side closer to the objective lens than the focal point of the objective lens (position A shown in FIG. 17), and P1>P2 is established, the surface plasmon polariton is coupled to the evanescent wave of the wave number directed from the inside of the sensor chip to the outside. Thus, the surface plasmon polariton propagates from the inside of the sensor chip to the outside.

As stated above, in the sensor chip of the embodiment, the incident light is coupled to the surface plasmon polariton by the metal concave-convex structure formed on the chip surface. The surface plasmon polariton generates an intense localized electric field in the vicinity of the surface of the metal concave-convex structure. The metal concave-convex structure of the period P1 in the inside of the sensor chip causes a light having a vertical or approximately vertical angle component to be strongly coupled to the surface plasmon polariton. On the other hand, the concave-convex structure of the period P2 in the outside causes a light having an oblique angle component to be strongly coupled to the surface plasmon polariton. In this way, as compared with the comparative example, more light energy incident on the metal concave-convex structure can be coupled to the surface plasmon polariton.

Figure 7:
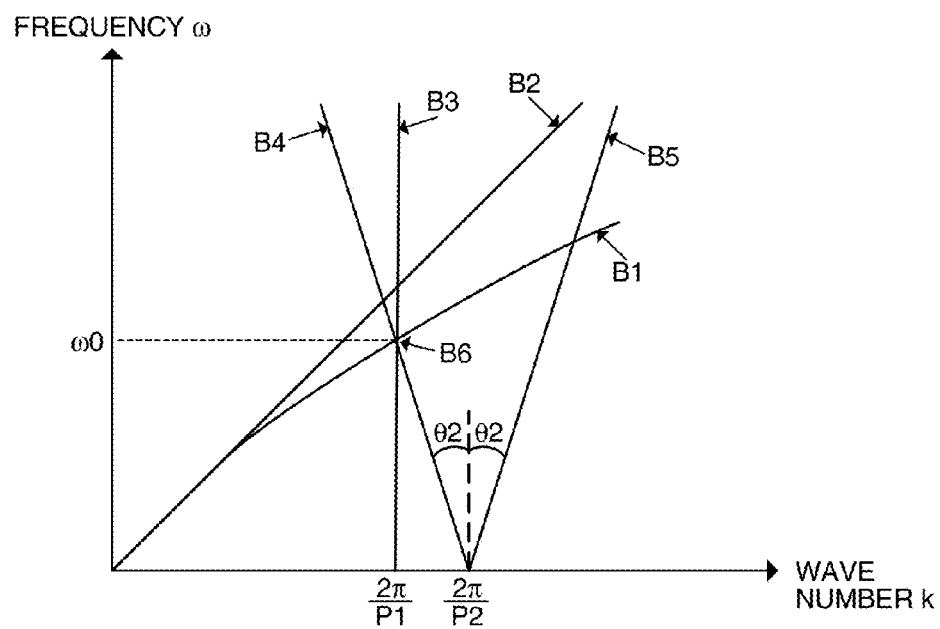
FIG. 7 is a dispersion curve of a surface plasmon polariton.

Next, a setting method of the periods P1 and P2 will be described. FIG. 7 shows a dispersion curve of surface plasmon polariton of the embodiment. Reference numeral B1 denotes a dispersion curve, B2 denotes a light line, B3 denotes a straight line representing a diffraction condition in the case of θ1=0°, and B4 and B5 denote straight lines representing diffraction conditions in the case of θ2>0°.

First, the dispersion curve B1 is obtained by RCWA (Rigorous Coupled Wave Analysis) (L. Li and C. W. Haggans, J. Opt. Soc. Am., A10, 1184-1189 (1993)). The dispersion curve B1 is a curve intrinsic to the kind of a metal, the kind of a medium, and the sectional shape of a metal grating. Next, the period P1 is set so that the straight line B3 passes through an intersection point B6 between a frequency ω=ω0 (angular frequency) of the incident light and the dispersion curve B1. As a result, the surface plasmon resonance can be generated for the incident light of the incident angle θ1. Next, the period P2 is set so that the straight line B4 (or the straight line B5) passes through the intersection point B6. That is, the period P2 is set so that $2\pi/P2 - kix = 2\pi/P1$ (or $2\pi/P2 + kix = 2\pi/P1$) is satisfied. As a result, the surface plasmon resonance can be generated for the incident light of the incident angle θ2 by the grating of the period P2. In this way, the two metal concave-convex structures can be made to have the same resonant wavelength.

As described above, in the surface plasmon resonance sensor using the metal periodic structure, since the surface plasmon resonance has a large selectivity to the incident angle of the incident light, there is a problem in that only a part of the light concentrated by the objective lens is coupled to the surface plasmon polariton.

With respect to this point, in the sensor chip (optical device) of the embodiment, a target is arranged on the metal grating 160 formed on the base member 100, and the target is detected by using the surface plasmon resonance and the surface-enhanced Raman scattering. The metal grating 160 (electrically conductive grating) includes the projection groups 110 and 120 made of the metal (electric conductor). The projection groups 110 and 120 are arranged at the period shorter than the wavelength λ1 of the incident light along the direction (for example, the direction D1 or the radial direction) parallel to the surface 130 (in a broad sense, virtual plane) of the base member 100. The period of the projection group includes at least the first period P1 and the second period P2 (P2≠P1) different from the first period P1.

In the above, although the example in which the sensor chip includes the metal grating 160 is described, this embodiment is not limited to this, and the sensor chip may only include the projection groups 110 and 120. That is, the metal grating 160 is an example of the periodic structure of the projection groups 110 and 120, and in this embodiment, it is not always necessary that the sensor chip is formed in the grating.

Here, the period of the projection group including at least the periods P1 and P2 may be a period including only the periods P1 and P2, or may be a period further including another period different from the periods P1 and P2. The virtual plane is a reference plane for the arrangement direction of the projection groups 110 and 120 and the incident angles θ1 and θ2 of the incident light, and is, for example, a surface parallel to the plane of the base member 100 (for example, the surface 130 of the base member 100).

As a result, the coupling efficiency of the incident light to the surface plasmon polariton can be improved. That is, as stated above, since the period of the projection group includes the periods P1 and P2, the incident lights having the different incident angles θ1 and θ2 can be coupled to the surface plasmon polariton at the same resonant wavelength λ1 (frequency ω0).

Specifically, in this embodiment, as shown in FIG. 5A, the metal grating 160 includes the first area R1 and the second area R2 adjacent to the first area R1. The first projection group 110 arranged at the first period P1 is provided in the first area R1, and the second projection group 120 arranged at the second period P2 is provided in the second area R2.

By doing this, the projection groups can be arranged in the areas R1 and R2 at the specific periods P1 and P2. As a result, the projection groups can be arranged at a period including at least the period P1 and the period P2 different from the period P1.

Further, in this embodiment, a first projection group arranged at a first variable period which increases or decreases stepwise from the first period P1 may be provided in the first area R1, and a second projection group arranged at a second variable period which increases or decreases stepwise from the second period P2 may be provided in the second area R2. For example, in the first area R1 and the second area R2, the period is not abruptly changed at a boundary between the regions (in accordance with the same regularity as that in the area), and the period of the first projection group and the second projection group may increase or decrease stepwise.

By doing this, the projection groups can be arranged at variable periods changing stepwise from the periods P1 and P2 in the areas R1 and R2. As a result, the projection groups can be arranged at a period including at least the period P1 and the period P2 different from the P1.

Here, the notion that the period increases or decreases stepwise means that the period increases or decreases every period or every plural periods. For example, the increase is a monotone increase, and the decrease is a monotone decrease. More specifically, when the variable period is Pj (j is a natural number), the incident angle of the incident light on the projection of the period Pj is θj, and θ1=0°, the period Pj increases or decreases so as to satisfy 2π/Pj −ki·sin θj=2π/P1 (or 2π/Pj+ki·sin θj=2π/P1).

In this embodiment, as shown in FIG. 6, for example, the incident light includes a light incident at a first angle θ1 with respect to the vertical line directed to the plane of the base member 100, and a light incident at a second angle θ2 different from the first angle θ1. The light incident at the first angle θ1 is incident on the first projection group 110 (projection group arranged at the first period P1), and the light incident at the second angle θ2 is incident on the second projection group 120 (projection group arranged at the second period P2). As shown in FIG. 7, the materials of the projection groups, the period P1 and the period P2 are set so that the resonant frequency (resonant wavelength) of the surface plasmon resonance in the first projection group 110 and that in the second projection group 120 become the same frequency ω0 (wavelength λ1).

\*\*\*By doing this, the materials of the projection groups, the period P1 and the period P2 can be set so that incident light having the different incident angles θ1 and θ2 are coupled to the surface plasmon polariton at the same resonant frequency ω0 (resonant wavelength λ1).

Further, in this embodiment, as shown in FIG. 6, the first period P1 is longer than the second period P2 (P1>P2). Also, in this embodiment, as shown in FIG. 14, the first period P1 may be shorter than the second period P2 (P1<P2).

Figure 9:
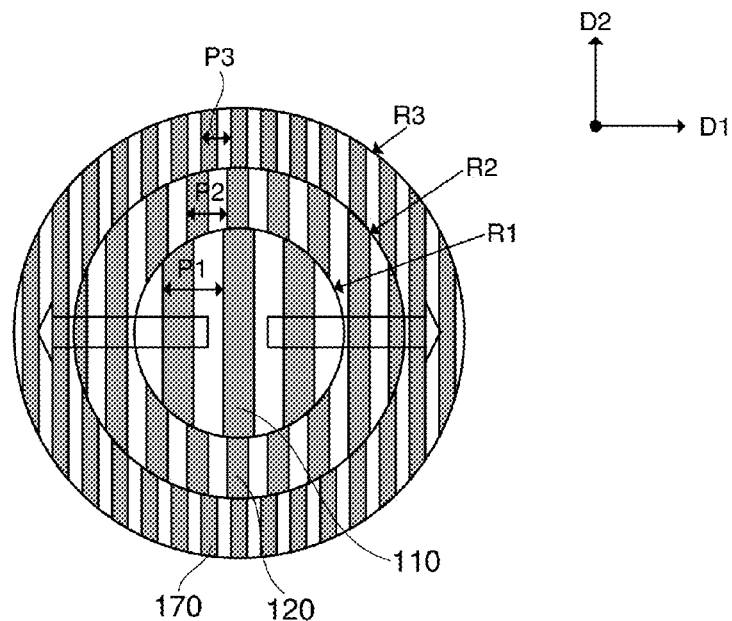
FIG. 9 shows a detailed structural example of a sensor chip.
Figure 11:
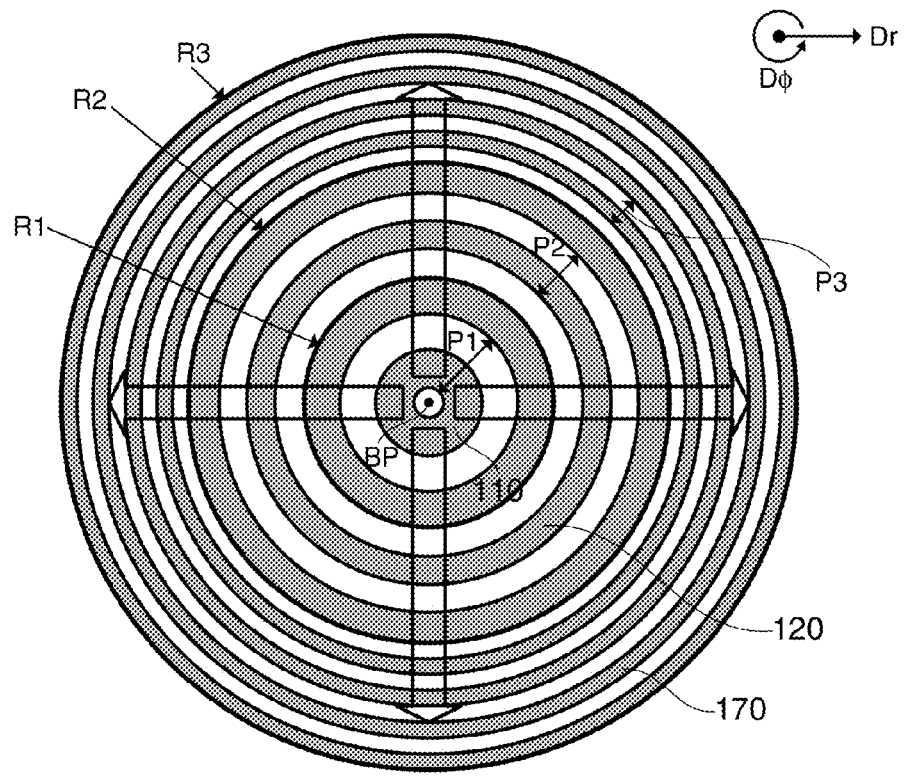
FIG. 11 shows a second structural example of a sensor chip.
Figure 17:
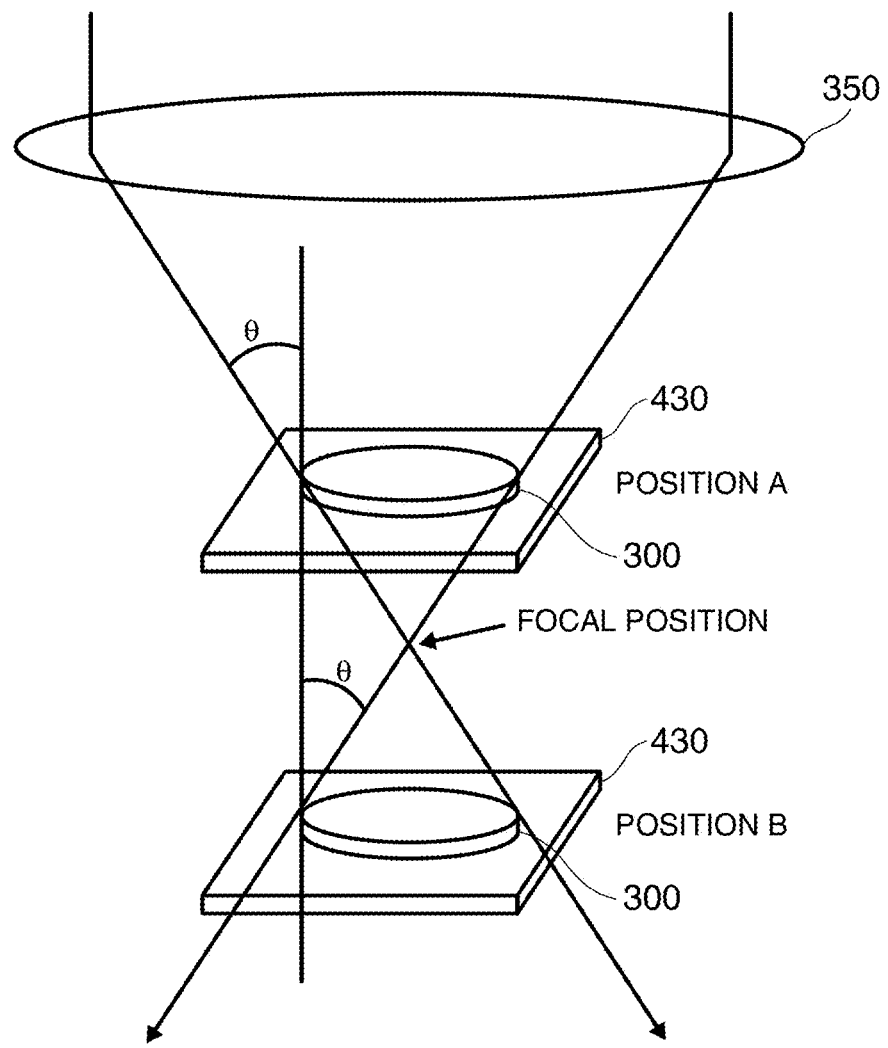
FIG. 17 is an explanatory view of an arrangement position of a sensor chip.

As stated above, when the magnitude relation between the inside period P1 and the outside period P2 of the sensor chip is reversed, the propagation direction of the surface plasmon polariton can be reversed. For example, as shown in FIG. 9 or FIG. 11, when the surface plasmon polariton propagates from the inside to the outside of the sensor chip, uniform enhanced electric field can be obtained on the entire surface of the sensor chip. When a target is rare, an attachment position of the target cannot be predicted. However, sensing independent of the attachment position can be performed by the uniform enhanced electric field. Incidentally, as shown in FIG. 17, the propagation direction of the surface plasmon polariton can be exchanged by changing the arrangement of the sensor chip.

Further, in this embodiment, the projection group is arranged in the same arrangement direction. For example, as shown in FIG. 5A, the projection group is arranged in the stripe shape (linear stripe), and the arrangement direction is the same straight line direction D1 over the entire strip-shaped arrangement. Alternatively, as shown in FIG. 11, the projection group is arranged concentrically, and the arrangement direction may be a radial direction (radius direction) of the concentric arrangement.

By doing this, the projection group can be arranged at the period including at least the first period P1 and the second period P2 different from the first period P1 (P2≠P1) along the direction parallel to the surface of the base member 100. In this embodiment, the metal grating 160 is not limited to the one-dimensional periodic structure, and a two-dimensional periodic structure may be adopted.

Figure 10:
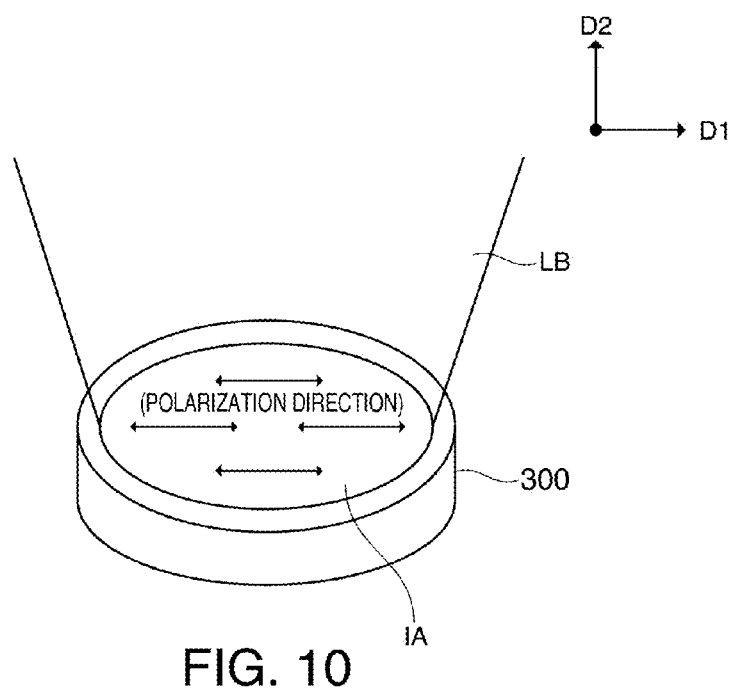
FIG. 10 shows an example of a polarization direction of a concentrated light beam when the projection group is arranged in a stripe shape.
Figure 12:
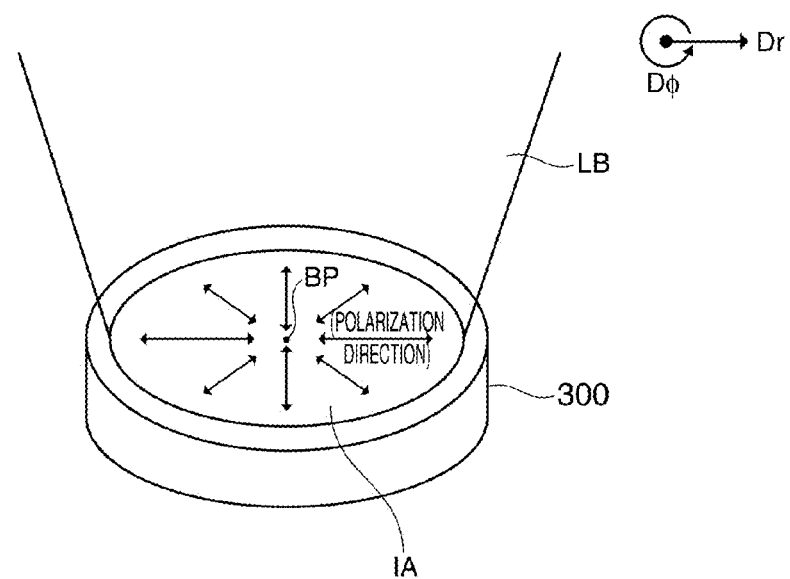
FIG. 12 shows an example of a polarization direction of a concentrated light beam when the projection group is concentrically arranged.

Further, in this embodiment, the arrangement direction of the projection group is the same direction as the polarization direction of the incident light. For example, as shown in FIG. 10, the incident light is a linearly polarized light, and the arrangement direction of the projection group is the same direction D1 as the polarization direction of the linearly polarized light. Alternatively, as shown in FIG. 12, the incident light is a radially polarized light, and the arrangement direction of the projection group may be the same direction (radius direction of the concentric circle) as the polarization direction of the radially polarized light.

By doing this, the projection group can be arranged in the same direction as the polarization direction of the incident light. As a result, a compression wave of free electron plasma is induced in the direction along the polarization direction by the incident light, and the surface plasmon propagating along the arrangement direction of the projection group can be excited. Incidentally, in this embodiment, the incident light may only include the linearly polarized light or the radially polarized light having the same polarization direction as the arrangement direction of the projection group. That is, no limitation is made to the incident light including only the same polarization direction as the arrangement direction of the projection group, and the incident light may include a polarized light having another polarization direction as long as the incident light includes the component having the same polarization direction as the arrangement direction of the projection group.

Figure 15:
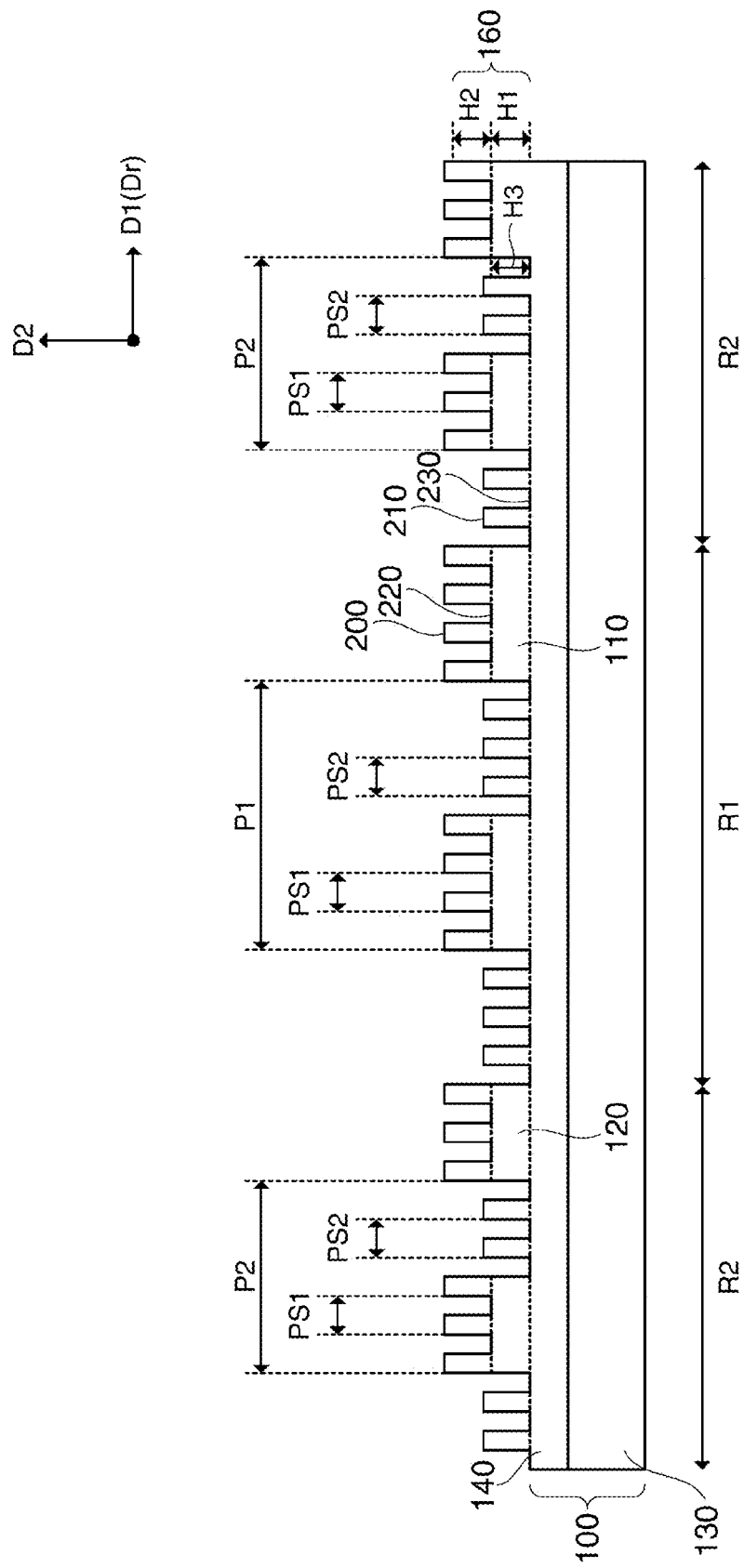
FIG. 15 is a sectional view of a third structural example of a sensor chip.

Further, in this embodiment, as shown in FIG. 15, a first small projection group 200 made of a metal may be provided on atop surface 220 of a projection group (for example, the first projection group 110 and the second projection group 120). The first small projection group is arranged at a first short period PS1 shorter than the period of the projection group including at least the first period P1 and the second period P2 and along the direction (the direction D1 or the radial direction) parallel to the plane of the base member 100.

Further, in this embodiment, as shown in FIG. 15, a second small projection group 210 made of a metal may be provided on a bottom 230 (surface parallel to the virtual plane and between the adjacent projections of the projection groups 110 and 120) between the adjacent projections of the projection groups. The second small projection group 210 is arranged at a second short period PS2 shorter than the period of the projection group including at least the first period P1 and the second period P2 and along the direction (the direction D1 or the radial direction) parallel to the plane of the base member 100.

In the above, although the description has been made of the case where the first small projection group 200 is arranged at the first short period PS1, and the second small projection group 210 is arranged at the second short period PS2, the embodiment is not limited to this. That is, it is not always necessary that the first small projection group 200 and the second small projection group 210 have this periodicity, and for example, the sizes of the projections in each group may have some variation.

By doing this, the propagation surface plasmon is excited by the projection groups 110 and 120, and the localized surface plasmon is excited in the first small projection group 200 and the second small projection group 210 by the propagation surface plasmon. As a result, electric field enhancement by the surface plasmon resonance can be further improved.

4. DETAILED STRUCTURAL EXAMPLE

The detailed structural example of the sensor chip will be described with reference to FIG. 8A to FIG. 10.

Figure 8A:
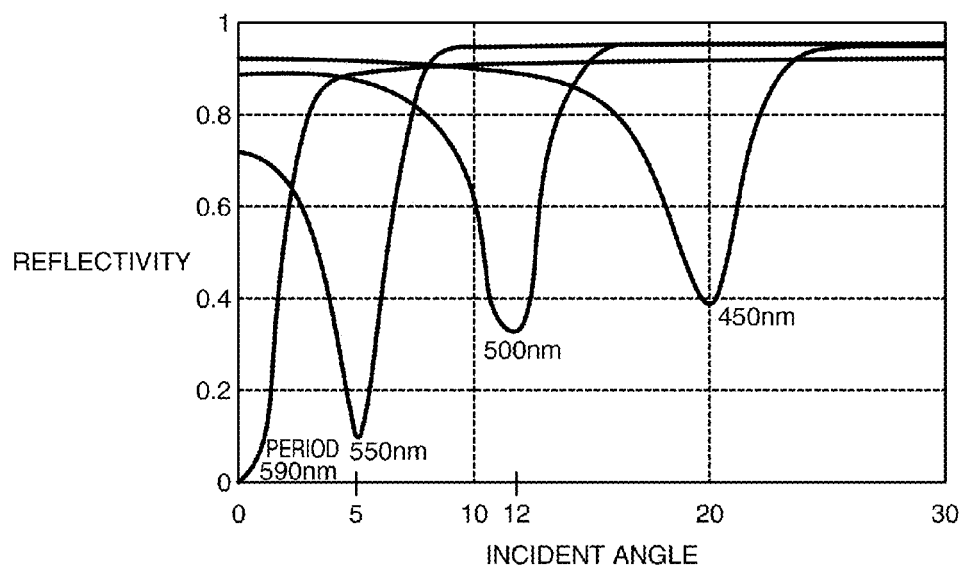
FIG. 8A and FIG. 8B show a characteristic example of reflected light intensity of a sensor chip with respect to light incident angle.
Figure 8B:
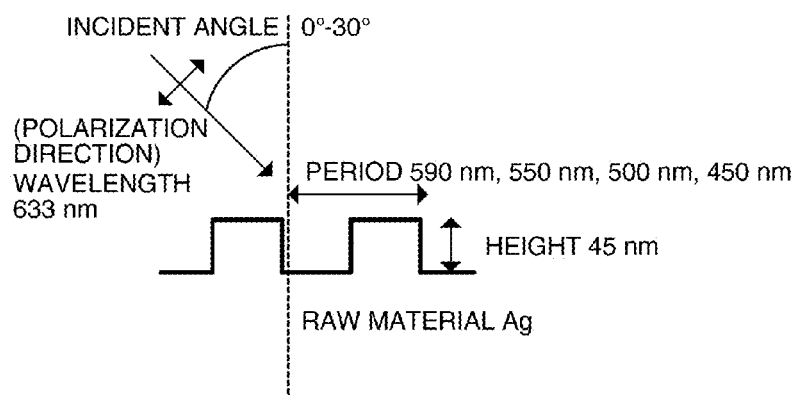

FIG. 8A shows a characteristic example of the reflected light intensity of the sensor chip with respect to the light incident angle. As shown in FIG. 8B, the material of the metal concave-convex structure is Ag, the sectional structure is rectangular, the height of the concave and convex is 45 nm, the excited wavelength is 633 nm, and the polarization direction is the direction perpendicular to the groove of the metal concave-convex structure. When the period of the metal concave-convex structure is 590 nm, 550 nm, 500 nm and 450 nm, the incident angle is changed within a range of 0° to 30°.

As shown in FIG. 8A, at the period of 590 nm, the surface plasmon resonance can be recognized under the condition where the light incident angle is 0°. Further, at the period of 550 nm, 500 nm and 450 nm, the surface plasmon resonance is recognized under the condition where the light incident angle is 5°, 12° and 20°.

Accordingly, in the sensor chip shown in FIG. 5A, when P1=590 nm and P2=500 nm are set, a concentrated light beam having an incident angle range of about ±15 degrees can be coupled to the surface plasmon polariton. This is equivalent to a case where the concentrated light beam is formed by using a lens of NA=0.2 (NA: numerical aperture). Further, as shown in FIG. 9, the number of the metal concave-convex structure groups is increased by one, and a third area R3 where a third projection group 170 is arranged at a period P3 may be provided outside the second area R2. When P1=590 nm, P2=500 nm and P3=450 nm are set, the concentrated light beam having an incident angle range of about ±25 degrees can be coupled to the surface plasmon polariton. This is equivalent to the case where the concentrated light beam is formed by using a lens of NA=0.4. As indicated by a thick arrow of FIG. 9, in the case of P1>P2>P3, the surface plasmon polariton propagates from the inside area R1 to the outside area R3 along the direction D1.

Incidentally, the size of the width of the resonant peak in the angle characteristic shown in FIG. 8A depends on the height of the metal concave-convex structure. When the structure is shallow, the resonant peak tends to become sharp and deep. When the structure is deep, the resonant peak tends to become wide and shallow. The number of the arranged metal concave-convex structures (the number of areas, the change width of the period) is determined in view of this point as well. As the angle range of the incident concentrated light beam becomes wide (NA of the light concentrating optical system becomes large), the number of the structures increases.

FIG. 10 shows an example of a polarization direction of a concentrated light beam when the projection group is arranged in a stripe shape. As shown in FIG. 10, a linearly polarized concentrated light beam LB is incident on a sensor chip 300. The linearly polarized light is polarized in the same polarization direction D1 on the entire surface of an incident area IA of the incident beam LB. As shown in FIG. 9, the polarization direction D1 is in the same direction as the arrangement direction D1 of the projection group. By doing this, free electrons in the metal grating are swung by an electric field oscillating in the polarization direction, and the surface plasmon propagating in the direction D1 is excited.

5. SECOND STRUCTURAL EXAMPLE

In the above embodiment, although the description has been made of the case where the metal concave-convex structure is arranged in the stripe shape, in this embodiment, metal concave-convex structures differing in period may be concentrically arranged. FIG. 11 shows a second structural example of such a sensor chip.

The metal grating of this sensor chip includes a first projection group 110, a second projection group 120, and a third projection group 170, which are concentrically arranged along a radius direction Dr (radial direction). The first projection group 110 is arranged at a first period P1 in a first area R1 including a center point BP (reference point) of the concentric circle. The second projection group 120 is arranged at a second period in a second area R2 outside the area R1. The third projection group 170 is arranged at a third period P3 in a third area R3 outside the second area R2. Each projection of the projection groups is formed into a circle whose center is the center point BP, and the sectional shape in the radius direction Dr is, for example, a rectangle. Incidentally, as indicated by a thick arrow of FIG. 11, in the case of P1>P2>P3, the excited surface plasmon polariton propagates from the center point BP of the concentric circle to the outside along the direction Dr.

Next, the function of the sensor chip will be described. In the sensor chip, incident light is coupled to the surface plasmon polariton by the concentric metal concave-convex structure formed on the chip surface, and intense localized electric field is generated in the vicinity of the surface of the metal concave-convex structure by the surface plasmon polariton. The metal concave-convex structure in the inside area R1 causes a light having a vertical and approximately vertical angle component to be strongly coupled to the surface plasmon polariton. On the other hand, the metal concave-convex structures in the outside areas R2 and R3 cause a light having oblique angle components to be strongly coupled to the surface plasmon polariton. In this way, as compared with the comparative example, more light energy incident on the metal concave-convex structure can be coupled to the surface plasmon polariton. Further, since the projection groups are concentrically arranged, resonance occurs independently of the rotation direction (direction Dφ shown in FIG. 13) when viewed in plane, and accordingly, the sensing sensitivity can be more improved.

FIG. 12 shows an example of the polarization direction of a concentrated light beam when the projection groups are concentrically arranged. As shown in FIG. 12, the concentrated light beam LB of radially polarized light is incident on the sensor chip 300. The radially polarized light is the polarized light symmetrical with respect to the optical axis of an objective lens (first optical system), and in the incident area IA of the incident beam LB, the light is polarized in the radius direction Dr in which the center point BP of the concentric circle is the center. The polarization direction Dr is in the same direction as the arrangement direction Dr of the projection group. By doing this, free electrons in the metal grating are swung by the electric field oscillating in the polarization direction, and the surface plasmon propagating in the direction Dr is excited.

6. MODIFIED EXAMPLE

Figure 13:
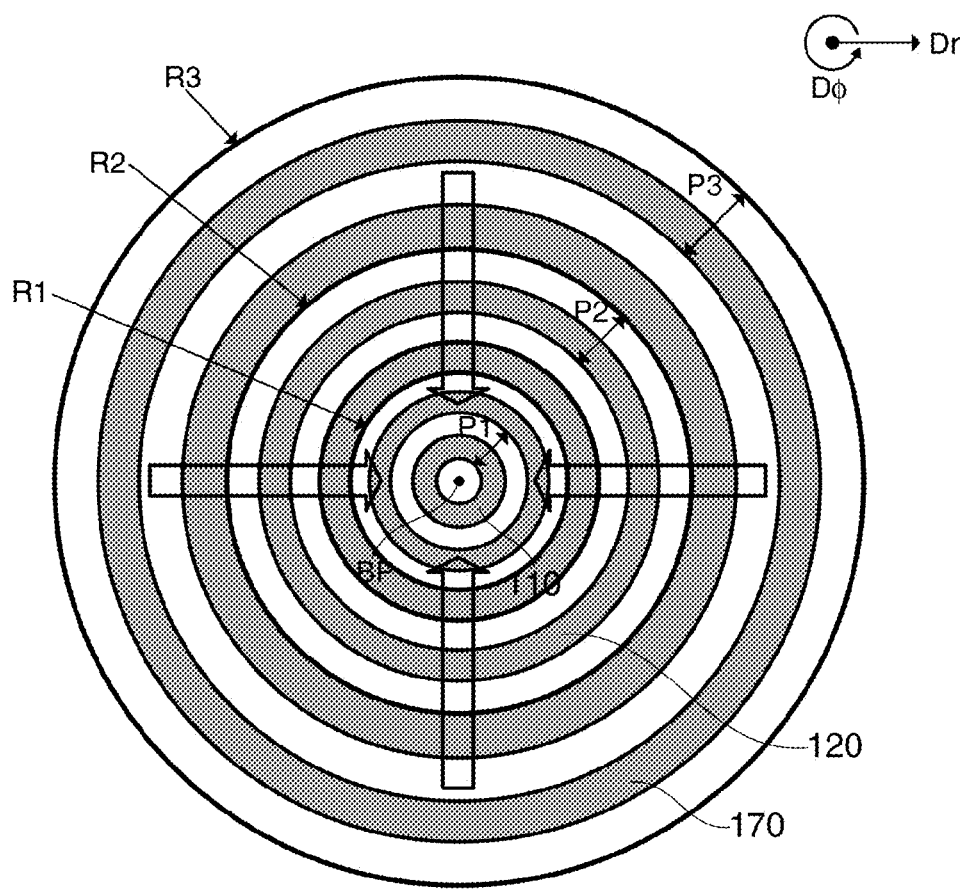
FIG. 13 shows a modified example of a sensor chip.

In the above embodiment, although the case of P1>P2>P3 is described, in this embodiment, as shown in FIG. 13, P1<P2<P3 may be adopted. In this case, as indicated by thick arrows, the surface plasmon polariton propagates from the outside of the concentric circle to the center point BP along the direction Dr.

The propagation direction will be specifically described with reference to FIG. 14. FIG. 14 is a schematic explanatory view of surface plasmon resonance in the case of P1<P2. Incidentally, in the following, only P1 and P2 will be described for simplification.

As shown in FIG. 14, an evanescent wave of wave number $2\pi/P1$ is generated in the grating of the period P1, and an evanescent wave of wave number $2\pi/P2\pm kix$ is generated in the grating of the period P2. In the case of P1<P2, the periods P1 and P2 are set so as to satisfy $2\pi/P2+kix=2\pi/P1$. Then, the surface plasmon polariton is coupled to the evanescent wave of the wave number directed from the outside to the inside of the sensor chip. Thus, the surface plasmon polariton propagates from the outside to the inside of the sensor chip.

7. THIRD STRUCTURAL EXAMPLE

In the above embodiment, although the propagation surface plasmon polariton is excited by the projection group, in this embodiment, the diffraction grating may include another projection group to excite a localized surface plasmon. FIG. 15 is a sectional view of a third structural example of a sensor chip.

The sensor chip includes a base member 100, a first projection group 110, a second projection group 120, a first small projection group 200, and a second small projection group 210. Incidentally, in the following, the same component as the component explained in FIG. 5B is denoted by the same reference numeral, and its explanation is suitably omitted.

As shown in FIG. 15, the first small projection group 200 is periodically arranged on a top surface 220 of the first projection group 110 and the second projection group 120 (hereinafter referred to as the projection group) along the arrangement direction D1 (or the direction Dr) of the projection group. The second small projection group 210 is periodically arranged on a bottom 230 between the projections of the projection group along the arrangement direction D1 (or the direction Dr) of the projection group.

More specifically, the first small projection group 200 has a height H2 from the top surface 220, and is arranged at a first short period PS1 shorter than the periods P1 and P2 of the projection groups. The second small projection group 210 has a height H3 from the bottom 230, and is arranged at a second short period PS2 shorter than the periods P1 and P2 of the projection groups. For example, it is preferable that the periods PS1 and PS2 are set to be 500 nm or less, and it is preferable that the heights H2 and H3 are set to be 200 nm or less. Incidentally, the height H3 may be H3>H1, or may be H3≤H1.

The sectional shape of each projection of the first small projection group 200 and the second small projection group 210 (hereinafter referred to as the small projection group) is formed into a convex shape from the top surface 220 and the bottom 230 in the section of the small projection group in the arrangement direction D1. The convex shape is a rectangle, trapezoid, arc or the like. For example, as shown in FIG. 5A, when the projection group is formed into a stripe shape, the small projection group is formed into a stripe shape parallel to the projection group. Alternatively, as shown in FIG. 11, when the projection group is formed concentrically, the small projection group is formed into a concentric shape whose center is the center point BP of the projection group. The small projection group may be made of the same material as the projection group, or may be made of a different material.

Incidentally, in the above, although the arrangement direction of the small projection group is equal to the arrangement direction of the projection group, in this embodiment, the arrangement direction of the small projection group may be different from the arrangement direction of the projection group. In this case, the arrangement periods PS1 and PS2 are arrangement periods in the direction D1.

Next, surface-enhanced Raman scattering by the sensor chip of the third structural example will be described. In this embodiment, the excited light is concentrated and made incident on the sensor chip. Then, as described above, the propagation surface plasmon is excited by the projection group. The surface plasmon propagates along the surface of the metal grating 160, and excites the localized surface plasmon in the small projection group. Then, the localized surface plasmon excites an enhanced electric field between the projections of the small projection group, and the surface-enhanced Raman scattering is caused by the mutual action between the enhanced electric field and a target. At this time, since the interval between the projections of the small projection group is narrow, the high enhanced electric field is excited between the projections. Thus, even if the number of targets attached between the projections is one or just a few, high surface-enhanced Raman scattering can be caused by the enhanced electric field.

8. ANALYZING APPARATUS

Figure 16:
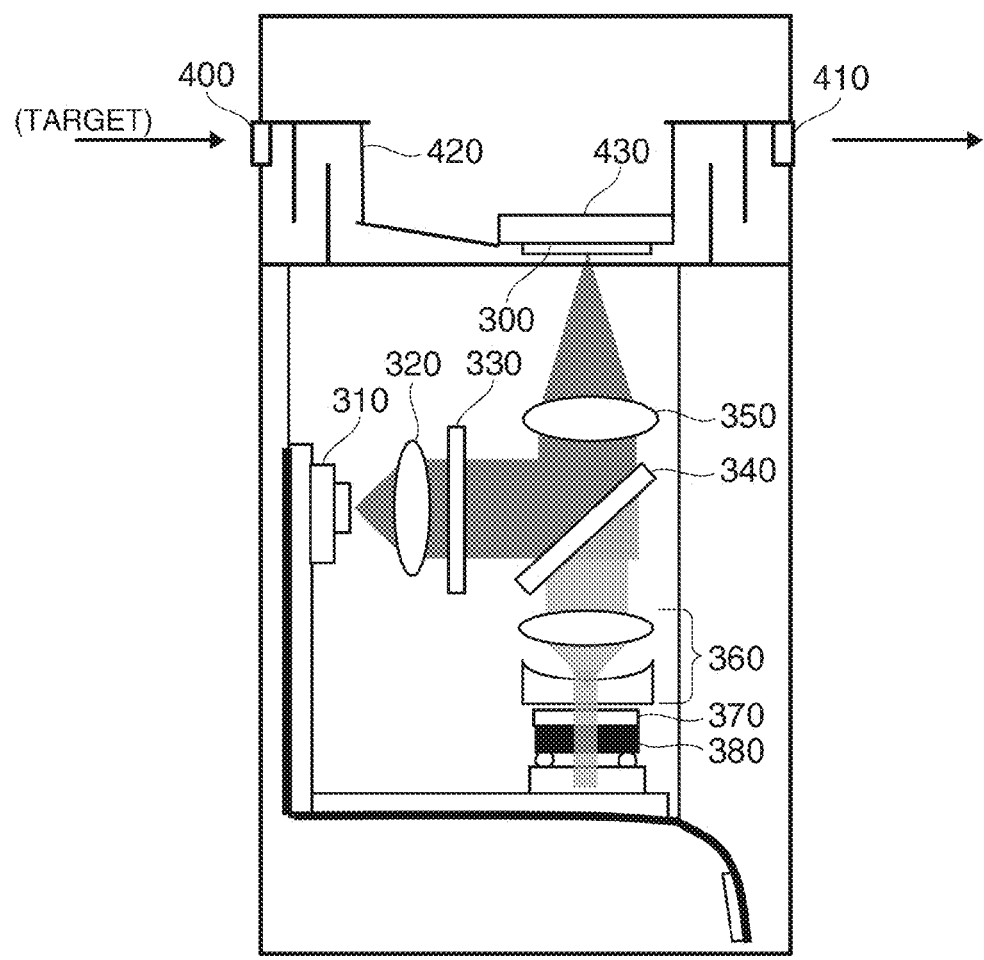
FIG. 16 shows a structural example of an analyzing apparatus.

FIG. 16 shows a structural example of an analyzing apparatus including the sensor chip of the embodiment. The analyzing apparatus (spectral apparatus in a broad sense) includes a sensor chip 300 (optical device), a laser light source 310 (light source in a broad sense), a collimator lens 320, a polarization control element 330, an objective lens 350 (first optical system), a dichroic mirror 340, a condenser lens 360, an etalon 370 (340, 360 and 370 denote a second optical system in a broad sense), an optical detector 380 (detector), a conveyance part 420 and a support part 430. Incidentally, the analyzing apparatus of the embodiment is not limited to the structure of FIG. 16, and various modifications can be made, for example, a part (for example, the conveyance part) of the components is omitted, or another component is added.

The laser light source 310 emits a laser light to excite surface plasmon. The wavelength of the laser light is equal to the resonant wavelength of the sensor chip 300 and is, for example, 633 nm. The laser light emitted from the laser light source 310 is made collimated light by the collimator lens 320, and is made linearly polarized light (or radially polarized light) by the polarization control element 330. The laser light passing through the polarization control element 330 is guided to the sensor chip 300 by the dichroic mirror 340, is concentrated by the objective lens 350, and is incident on the sensor chip 300 supported by the support part 430. For example, a metal grating or a detection material selecting mechanism is formed on the surface of the sensor chip 300. The period of the metal grating is shorter than the wavelength of the laser light.

An arrow shown in FIG. 16 indicates a conveyance direction of a target. The target is introduced from a carry-in port 400 into the inside of the conveyance part 420 by controlling driving of a fan (not shown), and is discharged from a discharge port 410 to the outside of the conveyance part 420. At this time, a part of the target passing through the conveyance part 420 is attached to the sensor chip 300 supported by the support part 430, and the target (not shown) is arranged on the surface of the sensor chip 300.

When the laser light is incident on the metal grating surface, free electrons are resonant and oscillated by the oscillation of the laser light, and a very high enhanced electric field is generated through the surface plasmon polariton in the vicinity of the metal grating surface. For example, when one to several target materials approach the metal grating surface, surface-enhanced Raman scattering is generated from the target materials. Rayleigh scattering light and Raman scattering light from the sensor chip 300 pass through the objective lens 350, and are guided to the optical detector 380 by the dichroic mirror 340. The scattering light is concentrated by the condenser lens 360, passes through the etalon 370, and is incident on the light detector 380. The Raman scattering light is separated from the scattering light by the etalon 370, and the Raman scattering light is received by the optical detector 380. In this way, the scattering light is spectrally decomposed, and spectrum information of the target is obtained.

According to the analyzing apparatus, since the sensor chip 300 having the fine metal structures different in period is provided, the incident concentrated light beam having a certain angle range and the surface plasmon polariton can be efficiently coupled to each other. As a result, a surface plasmon resonance sensor with high efficiency and high sensitivity is realized, and the presence or absence of a target can be detected from the surface-enhanced Raman scattering spectrum. Further, since the sensor has high sensitivity, even when the concentration of a material to be measured is low, qualitative and quantitative measurement can be accurately performed. Further, since the sensor chip of the embodiment is of the thin film type and can be arranged in a narrow place, the analyzing apparatus can be miniaturized.

Incidentally, the analyzing apparatus of the embodiment can be widely applied to a sensing apparatus used for detection of narcotic drugs or explosive materials, medical or health diagnosis, and the detection of food. Further, the analyzing apparatus can be used as an affinity sensor to detect the presence or absence of adsorption of a material, such as the presence or absence of adsorption of antigen in antigen-antibody reaction.

9. ARRANGEMENT POSITION OF SENSOR CHIP

In the analyzing apparatus, the sensor chip 300 can be made removable. In that case, an additional mechanism such as an auto-focus mechanism is desired in order to align the surface of the sensor chip 300 with the light concentration surface (position deviated from the focal point) of a concentrated light beam.

With respect to this point, as shown in FIG. 17, an offset is provided above or below the focal point of the concentrated light beam, so that it is possible to eliminate the operation of aligning the sensor chip 300 with the concentrated surface at each time of attachment. Specifically, the sensor chip 300 is arranged at one of a position A closer to an objective lens 350 than the focal point (light condensing point) and a position B farther from the objective lens 350 than the focal point. As a result, the structure of the analyzing apparatus can be simplified.

When the arrangement of the sensor chip 300 is exchanged between the position A and the position B, even in the sensor chip 300 having the same periodic structure, the propagation direction of the surface plasmon polariton can be changed. For example, as shown in FIG. 11, in the case of the metal concave-convex structure of P1>P2>P3, when the sensor chip is placed at the position A before the focal point, the excited surface plasmon polariton propagates from the center to the outside. On the other hand, when the sensor chip is placed at the position B behind the focal point, the excited surface plasmon polariton propagates from the outside to the center.

In the sensing application of a metal nano-structure, it is not always necessary that the surface plasmon polariton is concentrated to the center of the sensor chip 300, and the intensity of the localized electric field is increased only at the center. This is because when the localized electric field is enhanced only at the center, the sensitivity uniformity of the sensor chip 300 or the reproducibility of sensing may be impaired. It is desirable that the structure of the metal concave-convex structure and the arrangement position are determined according to the usage of sensing, that is, what material is detected in what way and by considering the propagation direction of the surface plasmon polariton.

Here, as shown in FIG. 17, the concentrated light beam including the light beam coincident with the optical axis of the objective lens 350 is incident on the sensor chip 300. The objective lens 350 and the sensor chip 300 are arranged so that the optical axis of the objective lens 350 passes through the area R1 (the area R1 shown in FIG. 11) of the sensor chip 300. However, the embodiment is not limited to this case, and it is sufficient if the concentrated light beam having a certain incident angle range is incident on the sensor chip 300.

Although the embodiment has been described in detail, it would be easily understood for one of ordinary skill in the art that many modifications can be made without departing from the novel features and the effects of the invention. Accordingly, all such modifications are included within the scope of the invention. For example, in the specification and the drawings, a term (target material, concentrated light beam, metal grating, metal, etc.) described together with a comprehensive or synonymous different term (target, incident light, diffraction grating, conductor, etc.) at least once can be replaced by the different term in any portion of the specification or the drawings. Further, the structure and the operation of the optical device, the analyzing apparatus and the like are not limited to those described in the embodiment, and various modifications can be made.

What is claimed is:

1. An optical device comprising:
a first projection group and a second projection group that are electrically conductive projections and that are arranged along a direction parallel to a virtual plane, wherein
the first projection group is provided in a first area, and the second projection group is provided in a second area adjacent to the first area,
the first projection group is arranged at a first period, and the second projection group is arranged at a second period different from the first period,
the first period and the second period are shorter than a wavelength $\lambda 1$ of an incident light,
the incident light includes a first light that is incident on the first projection group at a first angle with respect to a vertical line directed to the virtual plane and a second light that is incident on the second projection group at a second angle different from the first angle with respect to the vertical line, and
a material of the first and second projection groups, the first and second periods, and the first and second angles are determined so as to make both a first resonant wavelength of first surface plasmon resonance at the first projection group and a second resonant wavelength of second surface plasmon resonance at the second projection group the wavelength $\lambda 1$.

2. The optical device according to claim 1, wherein the first projection group is arranged at a first variable period which changes stepwise from the first period, and the second projection group is arranged at a second variable period which changes stepwise from the second period.

3. The optical device according to claim 2, wherein the first period and the second period change stepwise between the first area and the second area.

4. The optical device according to claim 1, wherein the first period is longer than the second period.

5. The optical device according to claim 1, wherein the first period is shorter than the second period.

6. The optical device according to claim 1, wherein the first and second projection groups are arranged in the same arrangement direction.

7. The optical device according to claim 6, wherein
the first and second projection groups are arranged in a stripe shape, and
the arrangement direction of the first and second groups is the same linear direction over the entire stripe arrangement.

8. The optical device according to claim 6, wherein
the first and second projection groups are arranged concentrically, and
the arrangement direction of the first and second groups is a radial direction of the concentric arrangement.

9. The optical device according to claim 1, wherein arrangement directions of the first and second projection groups are the same as a polarization direction of the incident light.

10. The optical device according to claim 9, wherein
the incident light is a linearly polarized light, and
the arrangement directions of the first and second projection groups are equal to the polarization direction of the linearly polarized light.

11. The optical device according to claim 9, wherein
the incident light is a radially polarized light, and
the arrangement directions of the first and second projection groups are equal to the polarization direction of the radially polarized light.

12. The optical device according to claim 1, wherein
a first small projection group of electric conductors is provided on a top surface of the first projection group, and
an interval between projections in the first small projection group is shorter than the first period.

13. The optical device according to claim 1, wherein
a second small projection group of electric conductors is provided on a surface parallel to the virtual plane and between adjacent projections of the first and second projection groups, and
an interval between the projections in the second small projection group is shorter than the first and second periods.

14. An analyzing apparatus comprising:
a light source;
an optical device according to claim 1;
a first optical system that concentrates a light of the wavelength $\lambda 1$ from the light source to the first and second projection groups, and causes the first and second lights to be incident on the first and second projection groups, respectively;
a second optical system to extract Raman scattering light from light scattered or reflected by a diffraction grating of the optical device; and
a detector to detect the Raman scattering light received through the second optical system.

15. An analyzing apparatus comprising:
a light source;
an optical device according to claim 2;
a first optical system that concentrates a light of the wavelength $\lambda 1$ from the light source to the first and second projection groups, and causes the first and second lights to be incident on the first and second projection groups, respectively;
a second optical system to extract Raman scattering light from light scattered or reflected by a diffraction grating of the optical device; and
a detector to detect the Raman scattering light received through the second optical system.

16. An analyzing apparatus comprising:
a light source;
an optical device according to claim 3;
a first optical system that concentrates a light of the wavelength $\lambda 1$ from the light source to the first and second projection groups, and causes the first and second lights to be incident on the first and second projection groups, respectively;
a second optical system to extract Raman scattering light from light scattered or reflected by a diffraction grating of the optical device; and
a detector to detect the Raman scattering light received through the second optical system.

* * * * *